United States Patent
Henning et al.

(10) Patent No.: US 11,730,741 B2
(45) Date of Patent: Aug. 22, 2023

(54) 6-CHROMANOL DERIVATIVES FOR USE AS A MEDICAMENT

(71) Applicant: Sulfateq B.V., Groningen (NL)

(72) Inventors: Robert Henk Henning, Groningen (NL); Gerrit Jan Willem Euverink, Haren (NL); Guido Krenning, Groningen (NL); Adrianus Cornelis Van der Graaf, Groningen (NL)

(73) Assignee: SULFATEQ B.V., Groningen (NL)

( * ) Notice: Subject to any disclaimer, the term of this patent is extended or adjusted under 35 U.S.C. 154(b) by 0 days.

(21) Appl. No.: 16/640,761

(22) PCT Filed: Aug. 23, 2018

(86) PCT No.: PCT/EP2018/072734
§ 371 (c)(1),
(2) Date: Feb. 21, 2020

(87) PCT Pub. No.: WO2019/038360
PCT Pub. Date: Feb. 28, 2019

(65) Prior Publication Data
US 2020/0206235 A1    Jul. 2, 2020

(30) Foreign Application Priority Data

Aug. 25, 2017   (NL) .................................... 2019447

(51) Int. Cl.
*A61K 31/5377*   (2006.01)
*A61K 31/353*    (2006.01)
(Continued)

(52) U.S. Cl.
CPC ........ *A61K 31/5377* (2013.01); *A61K 31/353* (2013.01); *A61K 31/496* (2013.01); *A61K 9/0053* (2013.01)

(58) Field of Classification Search
CPC .............. A61K 31/5377; A61K 31/353; A61K 31/496; A61K 9/0053; A61K 31/4025;
(Continued)

(56) References Cited

U.S. PATENT DOCUMENTS

2017/0151234 A1*   6/2017   Van der Graaf ... A61K 31/5377

FOREIGN PATENT DOCUMENTS

EP          2935232 A1     10/2015
WO    WO 2014/098586 A1 *  6/2014
(Continued)

OTHER PUBLICATIONS

International Search Report for PCT/EP2018/072734 dated Dec. 3, 2018.
(Continued)

*Primary Examiner* — Taylor V Oh
(74) *Attorney, Agent, or Firm* — Hoyng Rokh Monegier B.V.; David P. Owen

(57) ABSTRACT

The present invention relates to the (S) enantiomeric form of certain 6-chromanol derivatives for use as a medicament. Especially, the present invention relates to the (S) enantiomeric form of a 6-chromanol derivative for use as a medicament wherein said 6-chromanol derivative is chosen from the group consisting of (6-hydroxy-2,5,7,8-tetramethylchroman-2-yl)(piperazin-1-yl)methanone; N-(benzyl)-6-hydroxy-2,5,7,8-tetramethylchroman-2-carboxamide; N-(phenyl)-6-hydroxy-2,5,7,8-tetramethylchroman-2-carboxamide; methyl 4-(6-hydroxy-2,5,7,8-tetramethylchroman-2-carboxamido)benzoate; (6-hydroxy-2,5,7,8-tetramethylchroman-2-yl)(morpholino)methanone, and pharmaceutically acceptable salts or bases thereof and pharmaceutically acceptable salts thereof.

4 Claims, 4 Drawing Sheets

Figure 1:
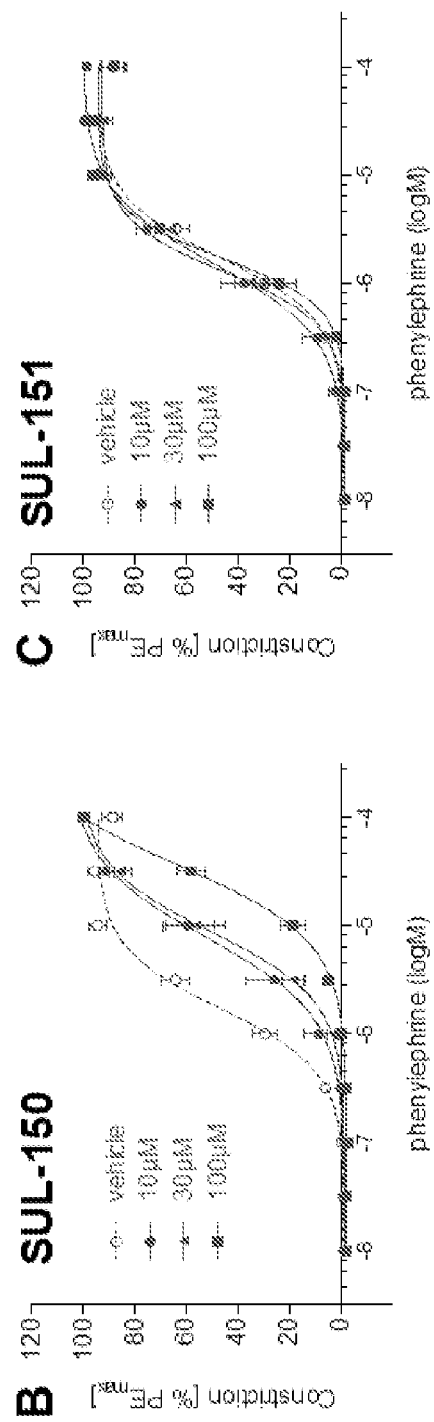

(51) Int. Cl.
*A61K 31/496* (2006.01)
*A61K 9/00* (2006.01)

(58) Field of Classification Search
CPC .......... C07D 311/72; A61P 3/08; A61P 39/06; A61P 29/00
USPC ...................................................... 514/233.5
See application file for complete search history.

(56) References Cited

FOREIGN PATENT DOCUMENTS

WO       20160188766 A1    12/2016
WO    WO2016/188766 A1 * 12/2016

OTHER PUBLICATIONS

International Preliminary Report on Patentability for PCT/EP2018/072734 dated Feb. 25, 2020.
Bing Han et al: "The anti-inflammatory and bronchodilating properties of the novel pharmacological compound Sul-121", internet citation, Apr. 24, 2015, p. 10.
Bing Han et al: "The novel compound Sul-121 inhibits airway inflammation and hyperresponsiveness in experimental models of chronic obstructive pulmonary disease", scientific reports, vol. 6, No. 1, May 27, 2016.

* cited by examiner

6-CHROMANOL DERIVATIVES FOR USE AS A MEDICAMENT

CROSS REFERENCE TO RELATED APPLICATIONS

This application is a 371 of PCT application number PCT/EP2018/072734 filed on Aug. 23, 2018, which claims priority from the Netherlands patent application number 2019447 filed on Aug. 25, 2017. All applications are hereby incorporated by reference in their entireties.

DESCRIPTION

The present invention relates to certain 6-hydroxy-2,5,7,8-tetramethylchroman compounds for the treatment or prophylaxis of diseases or disorders.

Certain chromanol compounds have been described in WO2014/098586, WO2015/193365 and WO2016/188766. These compounds show a wide variety of protective effects on cells and organs. The compounds described in detail are developed by Sulfateq, and have abbreviations, referring to SUL-XXX (XXX being a 2 or 3 digit number). Many of these compounds are racemic mixtures, although some enantiomers have been tested as well.

One of the compounds described in these references is SUL-121 (6-hydroxy-2,5,7,8-tetramethylchroman-2-yl)(piperazin-1-yl)methanone, which possesses strong anti-oxidant and inhibitory effects on airway hyper-responsiveness and inflammation. It was shown that SUL-121 dose-dependently reduced LPS-induced airway neutrophilia, LPS-induced attenuation of $H_2S$ production, neutrophilia-related as well as unrelated ROS production, and inhibited the nuclear translocation of the antioxidative response regulator Nrf2 in experimental in vivo models of COPD. The screening of a range of SUL compounds including trolox revealed that SUL-121 had a very potent anti-oxidant effect and confirmed cellular protection by SUL-121 in over 10 immortalized and 3 primary cell lines.

Taken together, these studies demonstrate that SUL compounds offer a range of protective effects against reactive oxygen species causing damage to lipids, proteins and DNA leading to increased inflammation and poor organ perfusion and subsequent organ failure, through a mechanism involving ROS scavenging, activation of mitochondrial complex I and IV and the maintenance of $H_2S$ production by transsulfuration enzymes cystathionine β-synthase (CBS) and cystathionine γ-lyase (CSE). Because of these useful properties, SUL compounds can be used in the prophylactis or treatment of a variety of disorders. As the mode of action is generally ROS scavenging, racemic mixtures are as effective as single enantiomers.

It is an object of the present invention to provide chromanol compounds for use in the prophylaxis or treatment of diseases or disorders, showing less side effects.

The above object is met, according to a first aspect, by the present invention by an (2S) enantiomeric form of certain 6-chromanol derivatives for use in the prophylaxis or treatment of diseases or disorders.

Thus, the present invention relates to the (2S) enantiomeric form of a 6-chromanol derivative for use as a medicament, wherein the 6-chromanol derivative is chosen from the group consisting of (6-hydroxy-2,5,7,8-tetramethylchroman-2-yl)(piperazin-1-yl)methanone (SUL-121); (6-hydroxy-2,5,7,8-tetramethylchroman-2-yl)(morpholino) methanone (SUL-95); N-(benzyl)-6-hydroxy-2,5,7,8-tetramethylchroman-2-carboxamide (SUL-96), N-(4-fluorobenzyl)-6-hydroxy-2,5,7,8-tetramethylchroman-2-carboxamide (SUL-97); 6-hydroxy-N—((S)-2-hydroxy-1-phenylethyl)-2,5,7,8-tetramethylchroman-2-carboxamide (SUL-98); N-(phenyl)-6-hydroxy-2,5,7,8-tetramethylchroman-2-carboxamide (SUL-103); 6-hydroxy-2,5,7,8-tetramethyl-N-(2-nitrophenyl)chroman-2-carboxamide (SUL-104); 6-hydroxy-2,5,7,8-tetramethyl-N-(3-nitrophenyl) chroman-2-carboxamide (SUL-105); N-(4-fluorophenyl)-6-hydroxy-2,5,7,8-tetramethylchroman-2-carboxamide (SUL-106); methyl 4-(6-hydroxy-2,5,7,8-tetramethylchroman-2-carboxamido)benzoate (SUL-107); N—((R)-2-amino-2-oxo-1-phenylethyl)-6-hydroxy-2,5,7,8-tetramethylchroman-2-carboxamide (SUL-111); (6-hydroxy-2,5,7,8-tetramethylchroman-2-yl)((S)-2-(hydroxymethyl)pyrrolidin-1-yl)methanone (SUL-112); 2-(((4-fluorobenzyl)amino)methyl)-2,5,7,8-tetramethylchroman-6-ol (SUL-116); 2-(((S)-2-(hydroxymethyl)pyrrolidin-1-yl) methyl)-2,5,7,8-tetramethylchroman-6-ol (SUL-128); 2-((((S)-2-hydroxy-1-phenylethyl)amino)methyl)-2,5,7,8-tetramethylchroman-6-ol (SUL-129); 2-(((S)-2-(hydroxymethyl)pyrrolidin-1-yl)methyl)-2,5,7,8-tetramethylchroman-6-ol (SUL-134); 2-(((R-2-(hydroxymethyl)pyrrolidin-1-yl) methyl)-2,5,7,8-tetramethylchroman-6-ol (SUL135); (6-hydroxy-5,7-diisopropyl-2,8-dimethylchroman-2-yl) (piperazin-1-yl)methanone (SUL-137); 1-(6-hydroxy-2,5,7,8-tetramethylchroman-2-carbonyl)-pyrrolidine-S-2-carboxylic acid (SUL-143) and pharmaceutically acceptable salts thereof.

In a preferred embodiment, the chromanol compound is chosen from the group consisting of the 2S enantiomer of (6-hydroxy-2,5,7,8-tetramethylchroman-2-yl)(piperazin-1-yl)methanone; N-(benzyl)-6-hydroxy-2,5,7,8-tetramethylchroman-2-carboxamide; methyl(6-hydroxy-2,5,7,8-tetramethyl-chroman-2-carboxamide)acetate; N-(phenyl)-6-hydroxy-2,5,7,8-tetramethylchroman-2-carboxamide; methyl 4-(6-hydroxy-2,5,7,8-tetramethylchroman-2-carboxamido)benzoate, and pharmaceutically acceptable salts thereof.

In another particularly preferred embodiment, the chromanol compound is chosen from the group consisting of the 2S enantiomer of (6-hydroxy-2,5,7,8-tetramethylchroman-2-yl)(morpholino)methanone, (6-hydroxy-2,5,7,8-tetramethylchroman-2-yl)(piperazin-1-yl)methanone and pharmaceutically acceptable salts thereof.

According to a most preferred embodiment, the present invention relates to the (2S) enantiomeric form of a 6-chromanol derivative, wherein said 6-chromanol derivative is (2S)(6-hydroxy-2,5,7,8-tetramethylchroman-2-yl)(piperazin-1-yl)methanone and pharmaceutically acceptable salts thereof.

SUL-121 is a 1:1 racemic mixture of two enantiomers (S enantiomer named SUL-151, R enantiomer named SUL-150). The effects of SUL-150 and SUL-151 on phenylephrine (PE)-induced vascular constrictions were investigated. The results showed that whereas SUL-150 exerted a dose-dependent increase of EC50, no significant effects after treatment with SUL-151 were observed. SUL-150 was able to inhibit or counteract the induced vascular constrictions, while SUL-151 did not exert any effect in these tests.

Unexpectedly, the SUL-151 compound did not have any effect on hemodynamic properties of mammals, like humans. This is important, because in the treatment of diabetes, COPD and the like, the pharmaceutically active compound preferably does not have an influence on other processes in the body, as such side effects would much complicate prescription practices.

It was found that the mechanism through which SUL-150 inhibits vasoconstriction is via direct interaction with the $\alpha_1$ adrenoceptor as a receptor antagonist. SUL-151 did not affect calcium transients in any of the investigated α1 adrenoceptor subtypes and therefore has less to no effect on the hemodynamic. Results indicate that SUL-150 is capable of counteracting vascular constriction and intracellular calcium responses specifically via its action on $\alpha_1$ adrenoceptors. Radiolabelled prazosin displacement suggests that SUL-150 competitively binds to the antagonist binding site. Prazosin is an $\alpha_1$-blocker which acts as an inverse agonist at alpha-1 adrenergic receptors. It was unexpected that SUL-151 did not show comparable results, making SUL-151 and analogous S-chromanol compounds excellent pharmaceutical active compounds for treating a variety of diseases or disorders, while keeping the hemodynamics completely unaltered.

Disorders, suitably treated with the 2S enantiomer of chromanols are disorders that require long (like lifelong) systemic treatment, like diabetes, lung disorders like asthma or COPD, or prophylactic treatment of organ damage that occur as secondary cause of disorders. Other disorders comprising inflammation as a symptom, for example include Cushing syndrome, kidney disorders, metabolic syndrome and the like.

The compounds are preferably used in effective amounts, to achieve a medical effect. Effects are observed with amounts of 0.5 μM, but preferably higher amounts are used. Preferred amounts are concentrations in vivo or in vitro of about 5 μM or higher, more preferably about 10 μM or higher. Generally, a concentration in human of about 200 μM or lower should be sufficient and safe.

For human use, this would mean—assuming a 30 L distribution volume, 100% availability and a concentration of about 0.5 μM—a dosage of about 5 mg or more. Preferred amounts would result in a concentration of about 5 μM—for which a dosage of about 50 mg or more would be suitable. Hence, preferably, dosage forms of about 20 mg or more, preferably 50 mg or more, preferably 100 mg or more are suitable. Generally, solid, oral dosage forms contain as a maximum about 500 mg compound, preferably about 450 mg or less, to allow for excipients. With i.v. other liquid forms of administration, larger amounts can be administered.

Examples of dosages which can be used are an effective amount of the compounds of the invention of a dosage of 0.1 mg/kg or higher, such as preferably within the range of about 0.5 mg/kg to about 100 mg/kg, or within about 1 mg/kg to about 40 mg/kg body weight, or within about 2 mg/kg to about 30 mg/kg body weight, or within about 3 mg/kg to about 15 mg/kg body weight. Compounds of the present invention may be administered in a single daily dose, or the total daily dosage may be administered in divided dosage of two, three or four times daily.

The compounds described herein can be formulated as pharmaceutical compositions by formulation with additives such as pharmaceutically or physiologically acceptable excipients carriers, and vehicles. Suitable pharmaceutically or physiologically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21" edition (2005).

A pharmaceutical composition can comprise a unit dose formulation, where the unit dose is a dose sufficient to have a therapeutic effect, preferably a therapeutic effect as described above. The unit dose may be a dose administered periodically in a course of treatment or suppression of a vasodilatory disorder.

Pharmaceutical compositions containing the compounds of the invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Time-release or controlled release delivery systems may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly (phosphoesters), poly amides, polyurethanes, poly(imidocarbonates) and poly(phosphazenes).

The compounds of the invention may be administered enterally, orally, parenterally, sublingually, by inhalation (e.g. as mists or sprays), rectally, or topically in dosage unit formulations containing conventional nontoxic pharmaceutically or physiologically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e.g. via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques. The compounds are mixed with pharmaceutically acceptable carriers, adjuvants, and vehicles appropriate for the desired route of administration.

Oral administration is a preferred route of administration, and formulations suitable for oral administration are preferred formulations.

The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols that are solid at room temperature but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The invention also provides articles of manufacture and kits containing materials useful for treating, preventing, or suppressing symptoms associated with medical conditions or disorders as described above. The article of manufacture comprises a container with a label. Suitable containers include, for example, bottles, vials, and test tubes. The containers may be formed from a variety of materials such as glass or plastic. The container holds a composition having an active agent which is effective for treating, preventing, or suppressing symptoms associated with a medical condition as described above. The active agent in the composition is one or more of the compounds of the invention. The label on the container preferably indicates that the composition is used for treating, preventing, or suppressing symptoms associated with a medical disorder or condition as described above, and may also indicate directions for either in vivo or in vitro use, such as those described above.

The invention also provides kits comprising any one or more of the compounds of the invention. In some embodiments, the kit of the invention comprises the container described above. In other embodiments, the kit of the invention comprises the container described above and a second container comprising a buffer. It may further include other materials desirable from a commercial and user standpoint, including other buffers, diluents, filters, needles, syringes, and package inserts with instructions for performing any methods described herein.

The amount of active ingredient that may be combined with the carrier materials to produce a single dosage form will vary depending upon the host to which the active ingredient is administered and the particular mode of administration. It will be understood, however, that the specific dose level for any particular patient will depend upon a variety of factors including the activity of the specific compound employed, the age, body weight, body area, body mass index (BMI), general health, sex, diet, time of administration, route of administration, rate of excretion, drug combination, and the type, progression, and severity of the particular disease undergoing therapy or condition to be treated. The unit dosage chosen is usually fabricated and administered to provide a defined final concentration of drug in the blood, tissues, organs, or other targeted region of the body. The effective amount for a given situation can be readily determined by routine experimentation and is within the skill and judgment of the ordinary clinician or skilled person.

The present invention will be further illustrated using the examples and figures below. In the examples, reference is made to figures wherein:

FIG. 1: Shows the constriction responses to phenylephrine (PE) in the presence of different doses of SUL-150 (B) and SUL-151 (C). Data is obtained from 2-3 experiments (n=4-6 per group). Constriction in graphics B and C is expressed as percentage of response to final PE addition.

Figure 2:
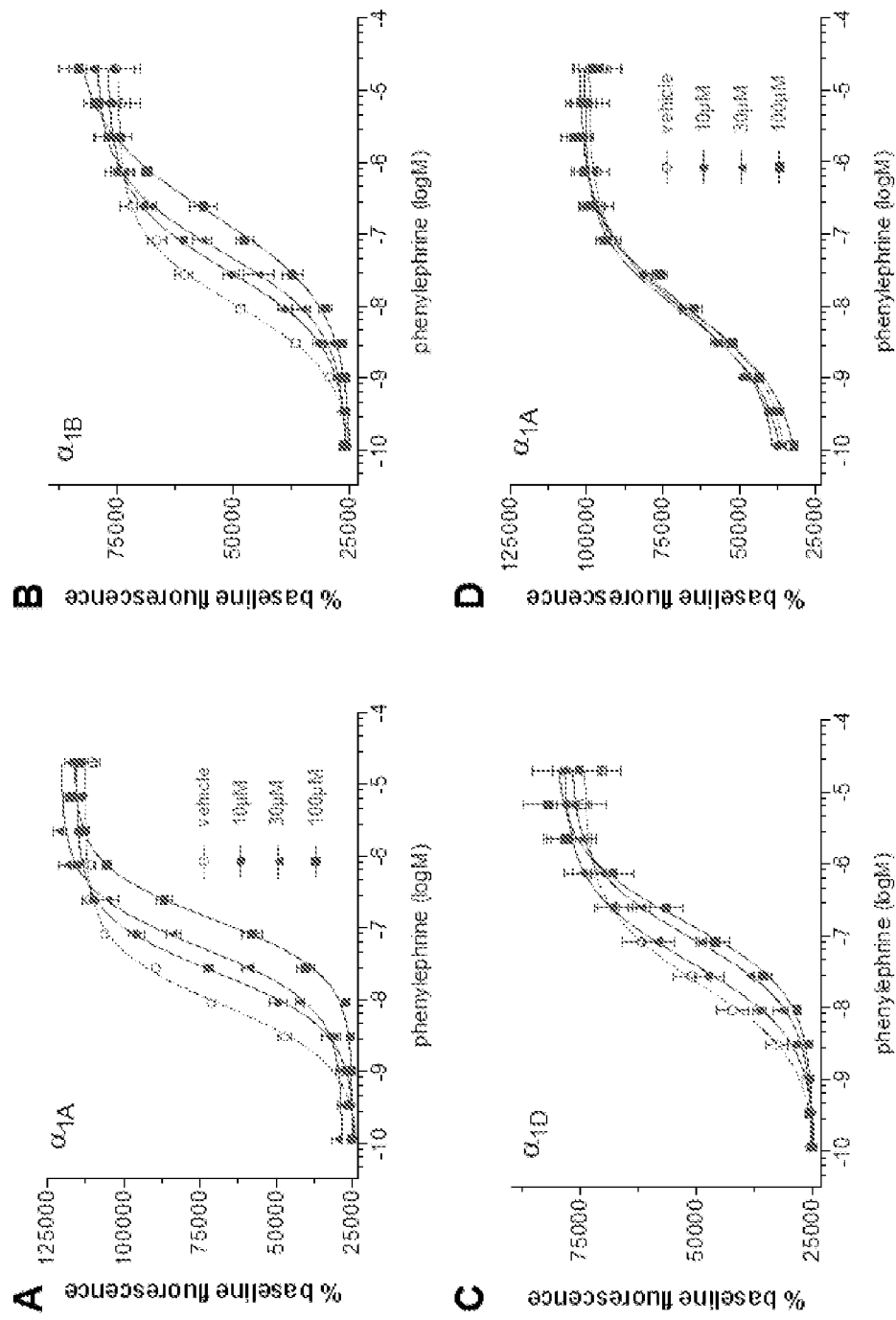

FIG. 2: Shows intracellular calcium measurements in transgenic CHO cells overexpressing $\alpha_1$ adrenoceptor subtypes A (A), B (B) and D (C) after stimulation with phenylephrine in the presence of vehicle (10% DMSO), 10 μM, 30 μM or 100 μM SUL-150. Figure D shows the effect of SUL-151 on the $\alpha_{1A}$ receptor.

Figure 3:
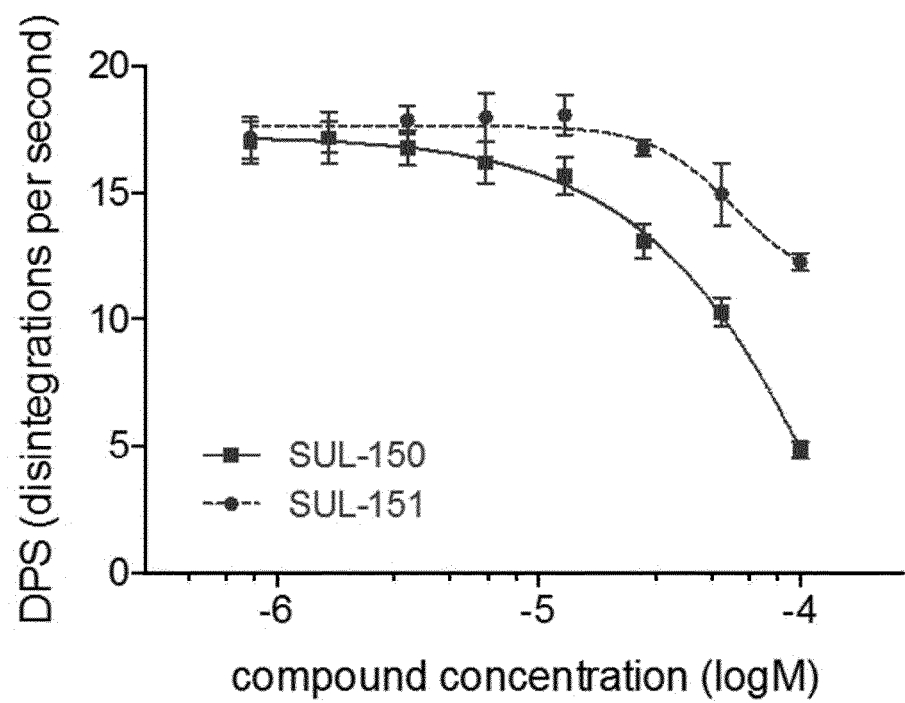

FIG. 3: Shows displacement of tritium-labelled prazosin by SUL-150 and SUL-151 in $\alpha_{1A}$ adrenoceptor transgenic CHO cells.

Figure 4:
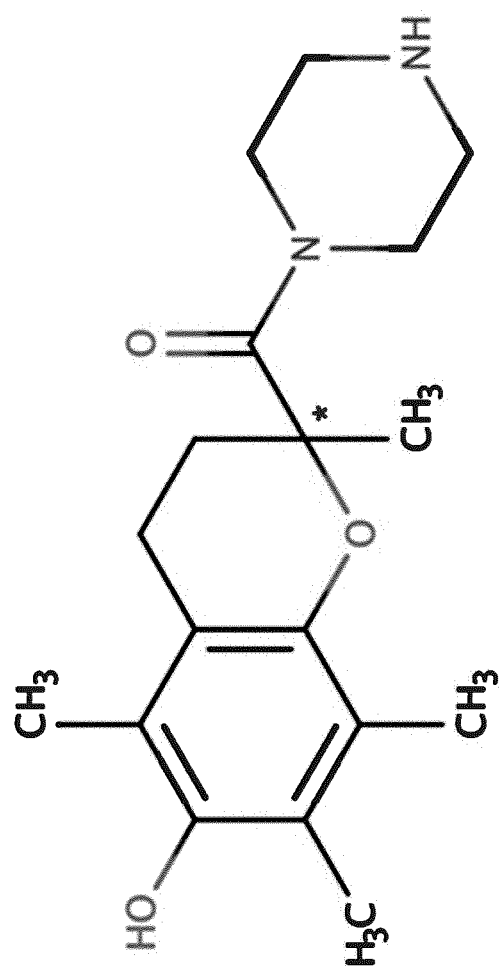

FIG. 4: Shows the structural formula of the SUL-121 ((6-hydroxy-2,5,7,8-tetramethylchroman-2-yl)-(piperaziniyl)-methanone) compound. SUL-121 is a racemic 1:1 mixture of (R)-enantiomer SUL-150 and (S)-enantiomer SUL-151. The*indicates the chiral centre of SUL-121 in the structural formula, which is at the 2 position in the chromanol group. Therefore, generally, the group of enantiomers is named the "2-S enantiomer of".

EXAMPLES

Example 1

Tissue Preparation and Myography in Isolated Porcine Renal Arteries

Porcine kidneys were obtained from a local slaughterhouse (Kroon Vlees, Gotenburgweg 30, 9723 ™ Groningen, The Netherlands) and transported on ice in normal physiological Krebs buffer containing 120 mM NaCl, 6 mM KCl, 2.5 mM $CaCl_2 \times 2H_2O$, 1.2 mM $MgCl_2 \times 6H_2O$, 1.2 mM $NaH_2PO_4 \times H_2O$, 25 mM $NaHCO_3$ and 11.4 mM D-(+)-Glucose monohydrate (all ingredients were purchased from Merck) in ultrapure water.

The renal artery tree was dissected from the kidney, cleaned of surrounding connective tissue and cut into equally-sized ring segments (2 mm in length). In some rings, endothelium denudation was performed by gentle rubbing of the intimal surface with a paper clip. Rings were mounted in organ baths as described previously (Buikema et al., 2000).

Arterial rings were washed thoroughly by replacing Krebs buffer and allowed to equilibrate for a period of 60 min under 1.4 g of resting tension before they were assessed for viability by inducing 2 subsequent constrictions with KCl (60 mM). Rings that failed to produce a threshold increase in diameter of 100 μm were excluded. After washout and stabilization, rings were treated for 30 minutes by incubation with vehicle (0.1% DMSO), SUL-121, SUL-150 or SUL-151, followed by subsequent incubation with cumulative doses of phenylephrine.

Dose-dependent constriction responses to phenylephrine ($10^{-8}$M-$10^{-4}$M) were recorded in isolated porcine intrarenal arteries. Buffer was warmed to 37° C. and aerated with 95% $O_2$ and 5% $CO_2$ before use.

Example 2

Cell Culture

CHO—K1 cells were stably transfected with a plasmid containing human $\alpha_1$-AR subtypes A, B and D in separate cell lines in DMEM-F12 medium with 10% FBS, 1% penicillin-streptomycin and 200 μg/mL Geneticin (G418, Invitrogen, Carlsbad, Calif.).

HeLa cells endogenously expressing histamine and TP receptors were grown in DMEM-F12 medium enriched with 10% FBS and 1% penicillin-streptomycin. Cells were kept in a tissue culture incubator at 37° C. in 5% $O_2$/95% $CO_2$ atmosphere and grown in 75 $cm^2$ non-treated cell culture flasks. Plating was performed 24 hours before measurement on black transparent-bottom 96-well plates at 20,000 cells per well density.

Intracellular Calcium Assays

On the next day, CHO cells were treated with either vehicle (0.1% DMSO) or SUL-150 resp. SUL-151 for 30 min at 37° C. and stimulated with a 3-fold dilution series of PE (20 μM-100 μM). $[Ca^{2+}]_i$ was measured using the fluorescent FLIPR Calcium 6 assay kit (Molecular Devices) in immortalized CHO cells stably expressing the $\alpha_1$ adrenoceptor.

Initially, calcium responses induced by non-cumulative concentration series of phenylephrine were investigated using fluorescent measurements in $\alpha_{1A}$ adrenoceptor-overexpressing CHO cells treated with SUL-150 and SUL-151 (FIG. 4). Fluorescent measurement data was processed and analyzed in SoftMax Pro 7 and expressed as % of baseline AUC with a 3-fold multiplier using an average of first 10 measurement points as baseline.

The "Vehicle" used in all experiments is 0.1% DMSO solution.

Data and Statistical Analysis

Vascular constriction responses are expressed as percentage of final response to KCl. Data are expressed as mean±SEM. *p<0.05.

Example 3

Induced Fit Molecular Docking Simulation

The binding of SUL-150 and SUL-151 to the antagonist binding site on the $\alpha_{1A}$-AR, induced fit molecular docking simulation was performed, using prazosin as a reference as follows.

The primary sequence of $\alpha_{1A}$ adrenoceptor was obtained from UniProt database (The UniProt Consortium, 2017) using reference code P35348 and uploaded to SWISS-MODEL in order to build a homology model, resulting in 373 templates. Subsequently, template ligand codes were used to query the PDB database to obtain structural data in SMILES format, which were processed by Chemmine to detect similarities with SUL-150. The SWISS-MODEL template that contained a ligand with the highest similarity score (a D3 dopamine receptor in complex with, Eticlopride, ETQ) was used to align the $\alpha_{1A}$-AR sequence onto a modelled backbone. The resulting homology model was validated by Ramachandran plot and prepared with Protein Preparation Wizard by the addition of hydrogens, bond order assignment, generation of partial charges to heteroatoms and disulfide bonds. Final refinement was performed by hydrogen bond assignment at pH 7.4 and restrained minimization at 0.3 RMSD.

Prazosin, SUL-150 and SUL-151 structural files were converted from SMILES to 3D structures using LigPrep. Protonation states were generated with Epik at pH 7.4 and small molecule energy parameters were computed using OPLS3 forcefield.

Flexible molecular docking simulation was performed using Induced Fit, part of the Schrödinger Small-Molecule Drug Discovery suite. A binding centroid was defined between residues involved in antagonist binding confirmed by mutagenesis (PHE312, PHE308 and ASP106) and ligands were docked within 15 Å, using an extended sampling protocol without constrains. Residues within 5 Å of resulting ligand poses were refined using Prime to improve ligand conformational sampling. Finally, the Scorpion server was used for the assessment and classification of small molecule-protein interactions and the final results were rendered using PyMOL 2.0.

Results

Effects of SUL-150 and SUL-151 on $\alpha_1$ Adrenoceptor Mediated Vasoconstriction To explore the effects of 2R and 2S-(6-hydroxy-2,5,7,8-tetramethylchroman-2-yl)(piperazin-1-yl)methanone (resp. SUL-150 and SUL-151) on constriction of isolated porcine intrarenal arteries, cumulative dose response curves to the $\alpha_1$ adrenoceptor agonist phenylephrine (PE) were constructed in the presence and absence of SUL-150 resp SUL-151 (FIG. 1). Whereas SUL-150 exerted a dose-dependent increase of $EC_{50}$ similar to SUL-121 (FIG. 1A, Table 1), we observed no significant effects after treatment with SUL-151 (FIG. 1B, Table 1).

TABLE 1

$LogEC_{50}$ values of phenylephrine-induced constriction responses in the presence of SUL-150 and SUL-151.

| logEC50 | phenylephrine | |
|---|---|---|
| | SUL-150 | SUL-151 |
| vehicle | −5.77 ± 0.04 | |
| 10 μM | −5.11 ± 0.09* | −5.82 ± 0.05 |
| 30 μM | −5.06 ± 0.06* | −5.89 ± 0.04# |
| 100 μM | −4.44 ± 0.09* | −5.77 ± 0.04 | p < 0.05 vs vehicle,
*p < 0.0001 vs vehicle

Effects of SUL-150 and SUL-151 on PE-Induced Intracellular Calcium Signalling

To further investigate the mechanisms through which SUL-150 inhibits $\alpha_1$ adrenoceptor mediated contractions, PE-induced calcium transients were studied in CHO cells stably overexpressing the human $\alpha_1$ adrenoceptor subtypes A, B and D. SUL-150 shifted dose response curves rightwards for all three $\alpha_1$ adrenoceptor subtypes (FIGS. 2A, B and C, Table 2). SUL-151 did not affect calcium transients in any of the investigated $\alpha_1$ adrenoceptor subtypes (only shown for the $\alpha_1$ adrenoceptor A subtype in FIG. 2D).

TABLE 2

LogEC$_{50}$ values of phenylephrine-induced calcium influx after treatment with SUL-150.

| logEC50 | SUL-150 | | | SUL-151 |
| --- | --- | --- | --- | --- |
| | α1A | α1B | α1D | α1A |
| vehicle | −8.07 ± 0.03 | −7.99 ± 0.08 | −7.68 ± 0.13 | −8.10 ± 0.11 |
| 10 μM | −7.62 ± 0.03* | −7.51 ± 0.08* | −7.37 ± 0.10 | −8.09 ± 0.10 |
| 30 μM | −7.28 ± 0.03* | −7.24 ± 0.07* | −7.04 ± 0.06* | −8.09 ± 0.11 |
| 100 μM | −6.88 ± 0.03* | −6.72 ± 0.08* | −6.80 ± 0.10* | −7.98 ± 0.10 |

*p < 0.0001 versus vehicle

Radioligand Binding Assay in α$_{1A}$ Adrenoceptor Overexpressing CHO Cells

SUL-150 affected PE-induced calcium transients, indicating that the effects of SUL-150 are upstream of calcium. We therefore explored whether SUL-150 could directly interact with the α$_1$ adrenoceptor as a receptor antagonist. For this, a displacement binding assay was performed on the α$_{1A}$ adrenoceptor transgenic CHO cells using radiolabeled prazosin, an established α$_{1A}$ adrenoceptor antagonist. SUL-150 was significantly more potent in displacing the radioligand compared to SUL-151, which displaced [7-Methoxy-3H]-prazosin only at concentrations higher than 10 μM (FIG. 3).

Induced Fit Molecular Modelling

Prazosin coexists in two protonation forms at pH 7.4. In the protonated form, the N1 assumes a positive charge, subsequently forming a salt bridge with the negatively charged side chain of ASP106, ultimately causing this form to assume an inverted orientation relative to its non-protonated form. The quinazoline scaffold of non-protonated prazosin was docked close to TM5 to form a confocal hydrogen bond between the 6,7-methoxy groups and SER188, a hydrogen bond between furan oxygen and SER83, and between prazosin carboxamide and GLN177 side chain; van der Waals interactions with side chains of PHE86, VAL107, ILE178, PHE289, MET292, and PHE312; π-π interactions with PHE288 and PHE312; and a π-hydrogen bond interaction with the side chain carboxy group and backbone peptide carboxamide of ASP106. The proposed binding mode of non-protonated prazosin indicated interactions which were in accord with those described in the literature.

An induced fit of SUL-150 and SUL-151 demonstrated alignment of the chromane scaffold with prazosin quinazoline, 6-hydroxy groups (SUL) and 6-metoxy (prazosin) as well as over their common piperazine moiety. Residues which were involved in forming contacts with all three compounds were VAL107, ILE178, SER188, PHE288, PHE289.

Glide scores computed using the Schrödinger Small-Drug Discovery Suite were −10.8 kcal×mol$^{-1}$, −10.2 kcal×mol$^{-1}$ and −9.4 kcal×mol$^{-1}$ for prazosin, SUL-150 and SUL-151 respectively. Prazosin and SUL-150 formed contacts with PHE312 and ASP106 confirmed in prazosin binding by mutagenesis, whereas SUL-151 did not show interactions with these residues. Additionally, the chirality of SUL-150 enables the orientation of its carboxamide towards ASN179, effectively forming a hydrogen bond. Additional hydrogen bond was formed between its protonated N-terminal and TYR316.

Comparison of the binding site-interactions of the several SUL compounds with the binding SUL-150, and the non-binding of SUL-151 and SUL-132 and SUL-138, allowed the prediction that the now claimed SUL-compounds indeed lack binding properties, whereas the R enantiomers would bind. Thus, the now claimed compounds do not show unwanted side effects of vascular restriction.

The invention claimed is:

1. Method for treating a disorder requiring long systemic treatment in a patient, comprising administering an (S) enantiomeric form of a 6-chromanol derivative, wherein said derivative is (2S)(6-hydroxy-2,5,7,8-tetramethylchroman-2-yl)(piperazin-1-yl)methanone or a pharmaceutically acceptable salt thereof, wherein the disorder is lung disorders, Cushing's syndrome, metabolic syndrome or organ damage that occur as secondary cause of the disorder, wherein said treatment does not have an effect on the hemodynamic behaviour of a patient.

2. The method for treating a disorder requiring long systemic treatment according to claim 1, wherein the 6-chromanol derivative is administered in an amount sufficient to achieve a concentration of 0.5 μM or higher.

3. The method for treating a disorder requiring long systemic treatment according to claim 2, wherein the 6-chromanol derivative is administered in an amount sufficient to achieve a concentration of about 5 μM or higher.

4. The method for treating a disorder requiring long systemic treatment according to claim 1, wherein said long treatment is lifelong treatment.

\* \* \* \* \*